United States Patent
McKinley et al.

(10) Patent No.: US 9,555,162 B2
(45) Date of Patent: Jan. 31, 2017

(54) PHOSPHOLIPID REDUCTION IN BIOLOGICAL TISSUE

(71) Applicant: Medtronic, Inc., Minneapolis, MN (US)

(72) Inventors: Laura McKinley, Costa Mesa, CA (US); Monique Poon, Tustin, CA (US); Will Wei Wang, Garden Grove, CA (US); Benjamin Wong, Irvine, CA (US)

(73) Assignee: Medtronic, Inc., Minneapolis, MN (US)

( * ) Notice: Subject to any disclaimer, the term of this patent is extended or adjusted under 35 U.S.C. 154(b) by 28 days.

(21) Appl. No.: 14/187,870

(22) Filed: Feb. 24, 2014

(65) Prior Publication Data

US 2015/0238658 A1 Aug. 27, 2015

(51) Int. Cl.
*A01N 1/00* (2006.01)
*A61L 27/36* (2006.01)

(52) U.S. Cl.
CPC ........ *A61L 27/3687* (2013.01); *A61L 27/3604* (2013.01); *A61L 27/3625* (2013.01); *A61L 2400/02* (2013.01); *A61L 2430/20* (2013.01); *A61L 2430/40* (2013.01)

(58) Field of Classification Search
CPC ............. A61L 27/3687; A61L 27/3604; A61L 2400/02; A61F 2/02
See application file for complete search history.

(56) References Cited

U.S. PATENT DOCUMENTS

| | | | |
|---|---|---|---|
| 4,885,005 A | | 12/1989 | Nashef et al. |
| 5,746,775 A | * | 5/1998 | Levy et al. .................. 8/94.11 |
| 6,479,079 B1 | * | 11/2002 | Pathak et al. ................ 424/520 |
| 7,989,157 B2 | | 8/2011 | Cunanan et al. |
| 8,007,992 B2 | * | 8/2011 | Tian et al. .................... 435/1.1 |

OTHER PUBLICATIONS

Vyavahare et al., Prevention of bioprosthetic heart valve calcification by ethanol preincubation. Circulation, vol. 95, (1997) pp. 479-488.*
Lim et al., Anticalcification effects of decellularization, solvent, and detoxification treatment for genipin and glutaraldehyde fixation of bovine pericardium. European Journal of Cardio-Thoracic Surgery, vol. 41, No. 2 (online Jun. 16, 2011) pp. 383-390.*
Cunanan et al., Tissue characterization and calcification potential of commercial bioprosthetic heart valves, Annals Thoracic Surgery, 2001; 71: S417-S421.

* cited by examiner

*Primary Examiner* — Kara Johnson

(57) ABSTRACT

A method of reducing phospholipid concentration in biological tissue. The biological tissue is immersed in an isopropyl alcohol solution for an effective period of time. After the effective period of time, the biological tissue has a phospholipid concentration that is at least 10 percent by weight less than an initial phospholipid concentration of the biological tissue.

18 Claims, 1 Drawing Sheet

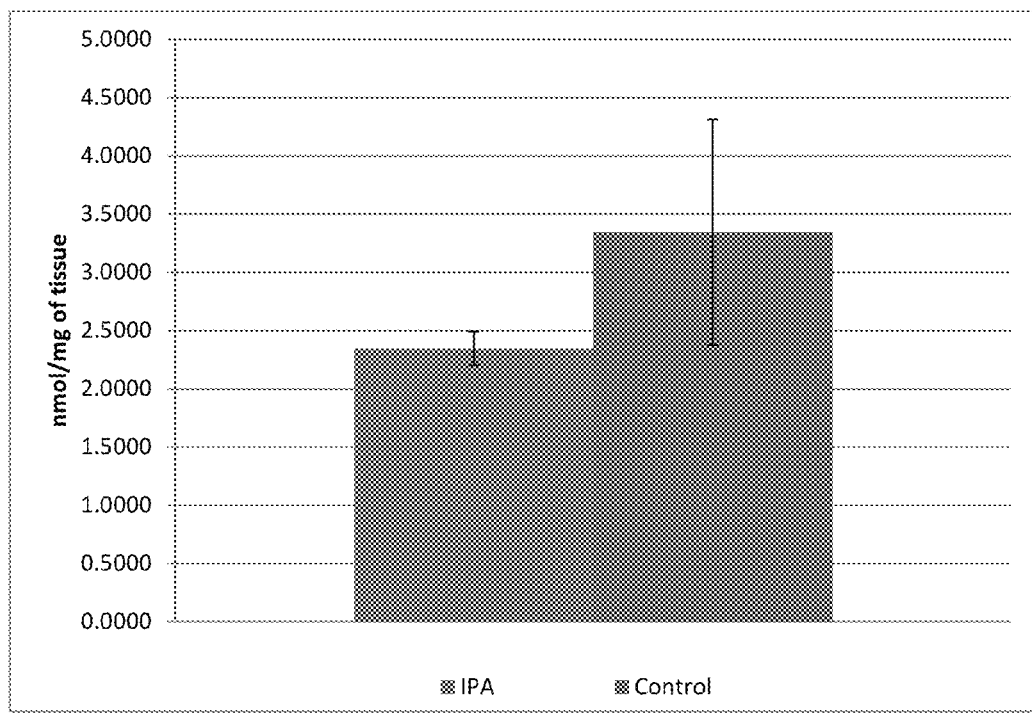

PHOSPHOLIPID REDUCTION IN BIOLOGICAL TISSUE

BACKGROUND

The invention is directed to a method of increasing the quality of biological tissue. More particularly, the invention relates to increasing the quality of biological tissue by reducing phospholipid concentration in the biological tissue.

Biological prostheses or "bioprostheses" are devices derived at least partially from processed biological tissues to be used for implantation into humans. Examples of bioprostheses that are currently used or in development include heart valves, vascular grafts, ligament substitutes, pericardial patches, and others.

Even though much is now known about biological tissue, bioprostheses and the processing, assembly, and performance thereof, there are still deficiencies that need to be overcome to provide a bioprostheses that preserves the native tissue properties while optimizing tissue biomechanics, minimizing calcification, and/or rendering the treated tissue hemocompatible.

For example, after harvesting from a donor, the biological tissue must be stored under proper conditions, and in proper solutions, to preserve the native properties of the tissue prior to and during the tissue processing steps that are to be subsequently undertaken. In addition, the harvested biological tissue should be stored in a manner that mitigates or even reduces the bioburden of the harvested tissue.

Further, the primary component of biological tissues used to fabricate many bioprostheses is collagen, a term used here in a generic sense to refer to a family of related extracellular proteins. Collagen molecules assemble to form microfibrils, which in turn assemble into fibrils, resulting in collagen fibers.

The amino acids that make up the collagen molecules contain side groups that represent sites for potential chemical reaction on these molecules. Because collagenous tissues degrade rapidly upon implantation into a host recipient, it is necessary to stabilize the tissue if it is to be used for long-term clinical applications. Chemical stabilization by cross-linking collagen molecules within the tissue (also known as tissue fixation) is well-known, and glutaraldehyde is commonly used to cross-link tissue.

Unfortunately, glutaraldehyde-fixed bioprosthetic tissues tend to become calcified over time. Calcification is undesirable because it results in undesirable stiffening or degradation of the implant.

The mechanism by which calcification occurs in glutaraldehyde-fixed bioprosthetic tissue has not been fully explained, and many factors have been thought to influence the rate of calcification.

In general, the calcification phenomenon has been characterized as being due to intrinsic causes (i.e., causes inherently contained within the tissue itself) and extrinsic causes (i.e., causes from outside the tissue itself, such as infection, patient's age, existing metabolic disorders, flow disturbances, etc.).

One intrinsic cause of calcification has been shown to be the presence of phospholipids in the harvested tissues. See e.g., Cunanan et al., Tissue characterization and calcification potential of commercial bioprosthetic heart valves, Annals Thoracic Surgery, 2001; 71: S417-S421. Therefore, it is desirable to mitigate or inhibit the calcification of the tissue to increase the usable life of any bioprostheses that is implanted into a human host.

Cunanan et al., U.S. Pat. No. 7,989,157, describes subjecting biological tissue to chemical fixation prior to the use of bioburden reduction solutions to extract phospholipids from the biological tissue. Cunanan indicates that the bioburden reduction solution may be a mixture of glutaraldehyde and polysorbate-80, such as is described in Nashef et al., U.S. Pat. No. 4,885,005.

SUMMARY

An embodiment of the invention is directed to a method of reducing phospholipid concentration in biological tissue. The biological tissue is immersed in an isopropyl alcohol solution for an effective period of time. After the effective period of time, the biological tissue has a phospholipid concentration that is at least 10 percent by weight less than an initial phospholipid concentration of the biological tissue.

Another embodiment of the invention is directed to a method of reducing phospholipid concentration in biological tissue. An organic solvent solution is prepared by mixing an organic solvent with water. The organic solvent is selected from the group consisting of isopropyl alcohol, acetone, ethanol and combinations thereof.

The biological tissue is immersed in the organic solvent solution for an effective period of time. After the effective period of time, the biological tissue has a phospholipid that is at least 10 percent less than an initial phospholipid concentration of the biological tissue.

BRIEF DESCRIPTION OF THE DRAWINGS

FIG. 1 is a chart that compares the phospholipid concentration in a pericardial tissue sample with isopropyl alcohol treatment to the phospholipid concentration without isopropyl alcohol treatment.

DETAILED DESCRIPTION

An embodiment of the invention is directed to a method of reducing phospholipid concentration in biological tissue. By reducing the phospholipid concentration, the calcification of the biological tissue is reduced.

Processing using the method described herein is done prior to the biological tissue being subjected to standard fixation processes such as chemical crosslinking. It is believed that utilizing the method at this stage facilitates removing a greater amount of phospholipids than after the fixation process because there is an enhanced ability of the solvent to penetrate the interstitial areas and thereby remove a greater portion of the phospholipids in the biological tissue before collagen fibers in the biological tissue are fixed, which tends to trap larger phospholipid molecules in the biological tissue.

Examples of types of biological tissue that may be used with the invention include porcine, bovine, equine, ovine, or other aortic or pulmonary valves and vascular tissues; human donor allografts; other sources of connective tissue matrices, including porcine, equine, ovine and other xenogeneic or allogeneic pericardial tissues; dura mater; omentum or other tissues of the digestive tract; skin, placenta, uterus, or tissues reconstructed in vitro from cells from such tissues; and ocular tissues including cornea and sclera.

Examples of other bioprostheses or devices that may be formed from biological tissue processed as described herein include heart valves and valve leaflets; vascular grafts for peripheral, coronary and dialysis access; patches, strips, or buckles used to reinforce or repair soft tissues, hard tissues, cartilage, tendon, cornea, or the like for organ repair and reinforcement for effective reconstruction procedures (including native valve reconstruction, valve annuloplasty and repair).

The methods may also be applied to create structures or devices for tissue augmentation procedures (including cardiac wraps, bands, or reinforcements for congestive heart failure, vascular aneurysm repair and reinforcement including cerebral, aortic, and abdominal devices), and as an adjunct or support for other devices fabricated from synthetic materials such as DACRON (polyethylene terephthalate, Invista, Wichita, Kans.) or PTFE; and scaffolds for repairing and/or regenerating tissues, either before or after implantation.

The phospholipid concentration of the biological tissue is reduced by immersing the biological tissue in an isopropyl alcohol solution for an effective period of time. After the biological tissue is immersed in the isopropyl alcohol solution for the effective period of time, the biological tissue has a phospholipid concentration of at least 10 percent less than an initial phospholipid concentration of the biological tissue.

In other embodiments, the treatment of the biological tissue in the isopropyl alcohol solution causes a reduction of the phospholipid concentration of between about 20 percent and about 40 percent. In still other embodiments, the treatment of the biological tissue in the isopropyl alcohol solution causes a reduction of the phospholipid concentration of between about 30 percent and about 35 percent.

In certain embodiments, the isopropyl alcohol solution contains a mixture of isopropyl alcohol and water. Increasing the concentration of isopropyl alcohol in the isopropyl alcohol solution decreases the amount of time that is needed to attain a particular reduction in the phospholipid concentration in the biological tissue.

On the other hand, increasing the concentration of isopropyl alcohol in the isopropyl alcohol solution increases the risk of damage to the tissue such as is caused by dehydration. In certain embodiments, the concentration of isopropyl alcohol in the isopropyl alcohol solution is sufficiently high so that the isopropyl alcohol inhibits bacterial growth on the biological tissue.

The isopropyl alcohol concentration in the isopropyl alcohol solution is greater than about 5 percent by weight. In certain embodiments, the isopropyl alcohol concentration in the isopropyl alcohol solution is between about 5 percent by weight and about 50 percent by weight.

In other embodiments, the isopropyl alcohol concentration in the isopropyl alcohol solution is between about 10 percent by weight and about 30 percent by weight. In still other embodiments, the isopropyl alcohol concentration in the isopropyl alcohol solution is about 20 percent by weight.

The isopropyl alcohol solution may also include a buffer that enhances the ability of the isopropyl alcohol solution to remain at a pH that is advantageous for the biological tissue. In certain embodiments, the buffer maintains the pH of the isopropyl alcohol solution between about 7.3 and 7.5.

In certain embodiments, the buffer may be isotonic. The buffer may include at least one of sodium chloride, potassium phosphate monobasic, sodium phosphate dibasic heptahydrate, hydrochloric acid and sodium hydroxide. In other embodiments, the buffer includes a mixture of a phosphate buffered solution and a chelating agent.

In other embodiments, an organic solvent solution is used instead of the isopropyl alcohol solution. The organic solvent solution should contain components that are not likely to damage the biological tissue during the phospholipid reduction process. Additionally, the components used in the organic solvent solution should not have the potential of exhibiting detrimental negative effects if such components remain associated with the biological tissue when the biological tissue is implanted in a living organism.

As such, the references to isopropyl alcohol solution in this application are intended to encompass organic solvent solution. The organic solvent solution contains water and at least one organic solvent selected from the group consisting of isopropyl alcohol, acetone, ethanol and combinations thereof.

The organic solvent concentration in the organic solvent solution is greater than about 5 percent by weight. In certain embodiments, the organic solvent concentration in the organic solvent solution is between about 5 percent by weight and about 50 percent by weight.

In other embodiments, the organic solvent concentration in the organic solvent solution is between about 10 percent by weight and about 30 percent by weight. In still other embodiments, the organic solvent concentration in the organic solvent solution is about 20 percent by weight.

The effective period of time in which the biological tissue is immersed may be affected by a variety of factors such as the concentration of the isopropyl alcohol in the isopropyl alcohol solution and the temperature of the isopropyl alcohol solution while the biological tissue is immersed therein.

In particular, the effective period of time is inversely rated to the concentration of isopropyl alcohol in the isopropyl alcohol solution. As such, as the concentration of isopropyl alcohol in the isopropyl alcohol solution increases, the effective period of time decreases.

The effective period of time is between about 1 hour when the isopropyl alcohol solution has an isopropyl alcohol concentration of about 90 percent by weight and about 120 hours when the isopropyl alcohol solution has an isopropyl alcohol concentration of about 5 percent by weight. When the isopropyl alcohol solution has an isopropyl alcohol concentration of about 20 percent by weight, the effective period of time is between about 48 hours and about 72 hours.

During the effective time in which the biological tissue is immersed in the isopropyl alcohol solution, the isopropyl alcohol solution may be maintained at a temperature of no more than 25° C. In other embodiments, the isopropyl alcohol solution may be maintained at a temperature of between about 4° C. and about 10° C. while the biological tissue is immersed in the isopropyl alcohol solution.

At least a portion of the isopropyl alcohol solution may be replaced while the biological tissue is immersed therein. Replacing the isopropyl alcohol solution may enhance the amount of phospholipid that is removed from the biological tissue. Replacing at least a portion of the isopropyl alcohol solution causes the isopropyl alcohol solution that is proximate the biological tissue to have a low phospholipid concentration.

Replacing at least a portion of the isopropyl alcohol solution may be done on a periodic basis or on a continuous basis. Replacement of the isopropyl alcohol solution may become increasingly important as the concentration of isopropyl alcohol in the isopropyl alcohol solution is decreased as such a process increases the amount of isopropyl alcohol that comes into contact with the biological tissue while the biological tissue is immersed therein.

In certain embodiments, at least about 50 percent by weight of the isopropyl alcohol solution is replaced while the biological tissue is immersed therein. In other embodiments, at least about 100 percent by weight of the isopropyl alcohol solution is replaced while the biological tissue is immersed therein.

At least one of the biological tissue and the isopropyl alcohol solution may be agitated while the biological tissue is immersed in the isopropyl alcohol solution. In certain embodiments, when the biological tissue and the isopropyl alcohol solution are placed in an enclosed container, both of the biological tissue and the isopropyl alcohol solution can be simultaneously agitated.

Agitating at least one of the biological tissue and the isopropyl alcohol solution enhances the amount of isopropyl alcohol that comes into contact with the biological tissue while the biological tissue is immersed therein. The movement of the isopropyl alcohol solution may cause the phospholipid that is at least partially liberated from the biological tissue to flow away from the biological tissue more quickly.

The phospholipid reduction method may be conducted by placing the isopropyl alcohol solution in an enclosed container. Using the enclosed container minimizes the evaporation of the components in the isopropyl alcohol solution during the process.

A portion of the enclosed container that is not occupied by the isopropyl alcohol solution and the immersed biological tissue may be filled with an inert gas. The inert gas may be selected from the group consisting of nitrogen, helium, neon, argon and combinations thereof.

Once the phospholipid reduction process is completed, the biological tissue may be subjected to a chemical fixation process such as using glutaraldehyde. Because the product produced from this process has a reduced phospholipid concentration compared to biological tissue that has not undergone phospholipid concentration reduction, the biological tissue exhibits reduced calcification, which thereby improves the durability of implants that incorporate the biological tissue.

The product and method of the present invention are described in the following examples. These examples are provided as an illustration of the invention and are not intended to limit the invention.

Example 1

Samples of pericardial tissue that had not undergone fixation were obtained. The pericardial tissue samples, which were weighed after fixation, had an average weight of 0.040 grams. An isopropyl alcohol solution was prepared by mixing about 20 percent by volume of isopropyl alcohol with phosphate buffered solution.

The pericardial tissue sample was immersed in about 1000 milliliters of the isopropyl alcohol solution for about 24 hours. While the pericardial tissue sample was immersed in the isopropyl alcohol solution, the isopropyl alcohol solution was maintained at a temperature of between about 4° C. and about 10° C.

The pericardial tissue sample was removed from the isopropyl alcohol solution after about 24 hours. The phospholipid concentration of 16 pericardial tissue samples was measured using colorimetric phospholipid assay and the average phospholipid concentration was about 2.3 nanomoles of phospholipid per milligram of the pericardial tissue. The result, which is identified as "IPA," is reported in FIG. 1.

Example 2

The process set forth in Example 1 was repeated with the exception of immersing the pericardial tissue in the isopropyl alcohol solution. The phospholipid concentration in 18 pericardial tissue samples was measured and the average phospholipid concentration was about 3.3 nanomoles of phospholipid per milligram of the pericardial tissue.

The result of this evaluation, which is identified as "Control," is reported in FIG. 1. The phospholipid concentration of the pericardial tissue prepared in Example 1 was about 30 percent lower than the phospholipid concentration of the pericardial tissue prepared in Example 2 (control).

Although the present disclosure has been described with reference to preferred embodiments, workers skilled in the art will recognize that changes can be made in form and detail without departing from the spirit and scope of the present disclosure.

What is claimed is:

1. A method of reducing phospholipid concentration in biological tissue comprising, prior to crosslinking of the biological tissue, immersing the biological tissue in an isopropyl alcohol solution for an effective period of time, wherein the isopropyl alcohol solution includes at least one organic solvent; wherein the total concentration of the at least one organic solvent in the isopropyl alcohol solution is about 5 to about 50 percent by weight; wherein the at least one organic solvent consists essentially of isopropyl alcohol, wherein after the effective period of time, the biological tissue has a phospholipid concentration that is at least 10 percent by weight less than an initial phospholipid concentration of the biological tissue.

2. The method of claim 1, wherein the biological tissue comprises heart valves, valve leaflets, vascular grafts, vascular patches, vascular strips, or vascular buckles, soft tissues, hard tissues, cartilage, tendon, cornea, or the like for organ repair and reinforcement for effective reconstruction procedures.

3. The method of claim 1, wherein a concentration of isopropyl alcohol in the isopropyl alcohol solution is between about 10 percent by weight and about 30 percent by weight.

4. The method of claim 1, wherein a concentration of isopropyl alcohol in the isopropyl alcohol solution is effective to inhibit bacterial growth on the biological tissue.

5. The method of claim 1, wherein the isopropyl alcohol solution further comprises a buffer.

6. The method of claim 1, and further comprising:
placing the isopropyl alcohol solution and the immersed biological tissue in an enclosed container; and
filling a portion of the enclosed container that is not occupied with the isopropyl alcohol solution and the immersed biological tissue with an inert gas.

7. The method of claim 6, wherein the inert gas is selected from the group consisting of nitrogen, helium, neon, argon and combinations thereof.

8. The method of claim 1, and further comprising maintaining the isopropyl alcohol solution at a temperature of between about 4° C. and 10° C. while the biological tissue is immersed in the isopropyl alcohol.

9. The method of claim 1, wherein the effective period of time is between about 12 hours and about 72 hours.

10. The method of claim 1, and further comprising replacing at least a portion of the isopropyl alcohol solution while the biological tissue is immersed in the isopropyl alcohol solution.

11. The method of claim 1, and further comprising agitating at least one of the biological tissue and the isopropyl alcohol solution while the biological tissue is immersed in the isopropyl alcohol solution.

12. A method of reducing phospholipid concentration in biological tissue comprising:

preparing an organic solvent solution by mixing about 5 to about 50 percent by weight of an organic solvent with water, wherein the organic solvent is selected from the group consisting of isopropyl alcohol, acetone, ethanol and combinations thereof; and prior to crosslinking of the biological tissue, immersing the biological tissue in the organic solvent solution for an effective period of time, wherein after the effective period of time, the biological tissue has a phospholipid that is at least 10 percent less than an initial phospholipid concentration of the biological tissue.

13. The method of claim 12, wherein a concentration of organic solvent in the organic solvent solution is between about 10 percent by weight and about 30 percent by weight.

14. The method of claim 12, wherein the organic solvent solution further comprises a buffer.

15. The method of claim 12, and further comprising maintaining the organic solvent solution at a temperature of between about 4° C. and 10° C. while the biological tissue is immersed in the organic solvent solution.

16. The method of claim 12, wherein the effective period of time is between about 12 hours and about 72 hours.

17. The method of claim 12, and further comprising replacing at least a portion of the organic solvent solution while the biological tissue is immersed in the organic solvent solution.

18. The method of claim 12, and further comprising agitating at least one of the biological tissue and the organic solvent solution while the biological tissue is immersed in the organic solvent solution.

\* \* \* \* \*